US008892400B2

(12) United States Patent
Wagner-Conrad et al.

(10) Patent No.: US 8,892,400 B2
(45) Date of Patent: Nov. 18, 2014

(54) METHOD FOR EVALUATING FLUORESCENCE CORRELATION SPECTROSCOPY MEASUREMENT DATA

(75) Inventors: Stephan Wagner-Conrad, Jena (DE); Yauheni Novikau, Jena (DE); Klaus Weisshart, Jena (DE)

(73) Assignee: Carl Zeiss Microscopy GmbH, Jena (DE)

(*) Notice: Subject to any disclaimer, the term of this patent is extended or adjusted under 35 U.S.C. 154(b) by 787 days.

(21) Appl. No.: 13/074,609

(22) Filed: Mar. 29, 2011

(65) Prior Publication Data

US 2011/0208478 A1   Aug. 25, 2011

Related U.S. Application Data

(63) Continuation of application No. PCT/EP2009/006819, filed on Sep. 22, 2009.

(30) Foreign Application Priority Data

Sep. 30, 2008   (DE) .................... 10 2008 049 877

(51) Int. Cl.
*G06F 11/34* (2006.01)
*G01B 7/004* (2006.01)
*G02B 21/00* (2006.01)
*G01N 21/64* (2006.01)

(52) U.S. Cl.
CPC .......... *G02B 21/0076* (2013.01); *G02B 21/008* (2013.01); *G01N 21/6458* (2013.01)
USPC ............. 702/179; 356/417; 702/40; 702/155; 702/182

(58) Field of Classification Search
CPC ............. G02B 21/0076; G02B 21/008; G01N 21/6458; G01N 2021/6417; G01J 3/4406
USPC .......... 702/40, 123, 150, 155, 179, 182, 183; 250/459.1, 461.2; 356/300, 317, 326, 356/417
See application file for complete search history.

(56) References Cited

U.S. PATENT DOCUMENTS 7,009,699 B2 * 3/2006 Wolleschensky et al. .... 356/317
7,154,602 B2 * 12/2006 Wachsmuth .................. 356/417
(Continued)

FOREIGN PATENT DOCUMENTS

DE   10 2007 052551 A1   5/2009
EP        1 593 957 A1   11/2005

OTHER PUBLICATIONS

Michelle A Digman: "Measuring Fast Dynamics in Solutions and Cells with a Laser Scanning Microscope," Biophysical Journal, vol. 89, No. 2, Aug. 30, 2005, pp. 1317-1327.

(Continued)

*Primary Examiner* — John H Le
(74) *Attorney, Agent, or Firm* — Westerman, Hattori, Daniels & Adrian, LLP

(57) ABSTRACT

With the different methods of fluorescence correlation spectroscopy, physical and biological transport processes in or between cells in the microscopic range, for example diffusion processes, can be analyzed. For this purpose, correlations of the fluorescence measurement data are determined for different sample regions and mathematical transport models are adapted thereto. Erroneous fluorescence correlation analyses were previously identified on the basis of the properties of the adapted model function parameters and were discarded. The a-priori knowledge necessary for the identification had to be obtained in time-consuming series of tests. With the invention, sample properties can be determined in a simpler, quicker and more exact way from fluorescence correlations. A suitability degree for one or more regions of the sample is determined for a correlation evaluation, describing quantitatively the information content of the respective region, or the error to be expected from a correlation evaluation, and can thus already be used before a correlation evaluation as a criterion for filtering/selecting the respective region. In this way, elaborate correlation calculations can be dispensed with in non-informative sample regions.

21 Claims, 7 Drawing Sheets

(56) References Cited

U.S. PATENT DOCUMENTS

2002/0044279 A1    4/2002  Khoury
2004/0257562 A1   12/2004  Wachsmuth
2010/0225910 A1    9/2010  Wagner-Conrad et al.

OTHER PUBLICATIONS

David L Kolin et al: "Advances in Image Correlation Spectroscopy: Measuring Number Densities, Aggregation States, and Dynamics of Fluorescently labeled Macromolecules in Cells" Cell Biochemistry and Biophysics, Totowa, NJ, US, vol. 49, Jan. 1, 2007, pp. 141-164.

Brown C M et al: "Raster image correlation spectroscopy (RICS) for measuring fast protein dynamics and concentrations with a commercial laser scanning confocal microscope," Journal of Microscopy, Wiley-Blackwell Publishing Ltd, GB, vo 1. 229, No. 1, Jan. 1, 2008, pp. 78-91.

\* cited by examiner

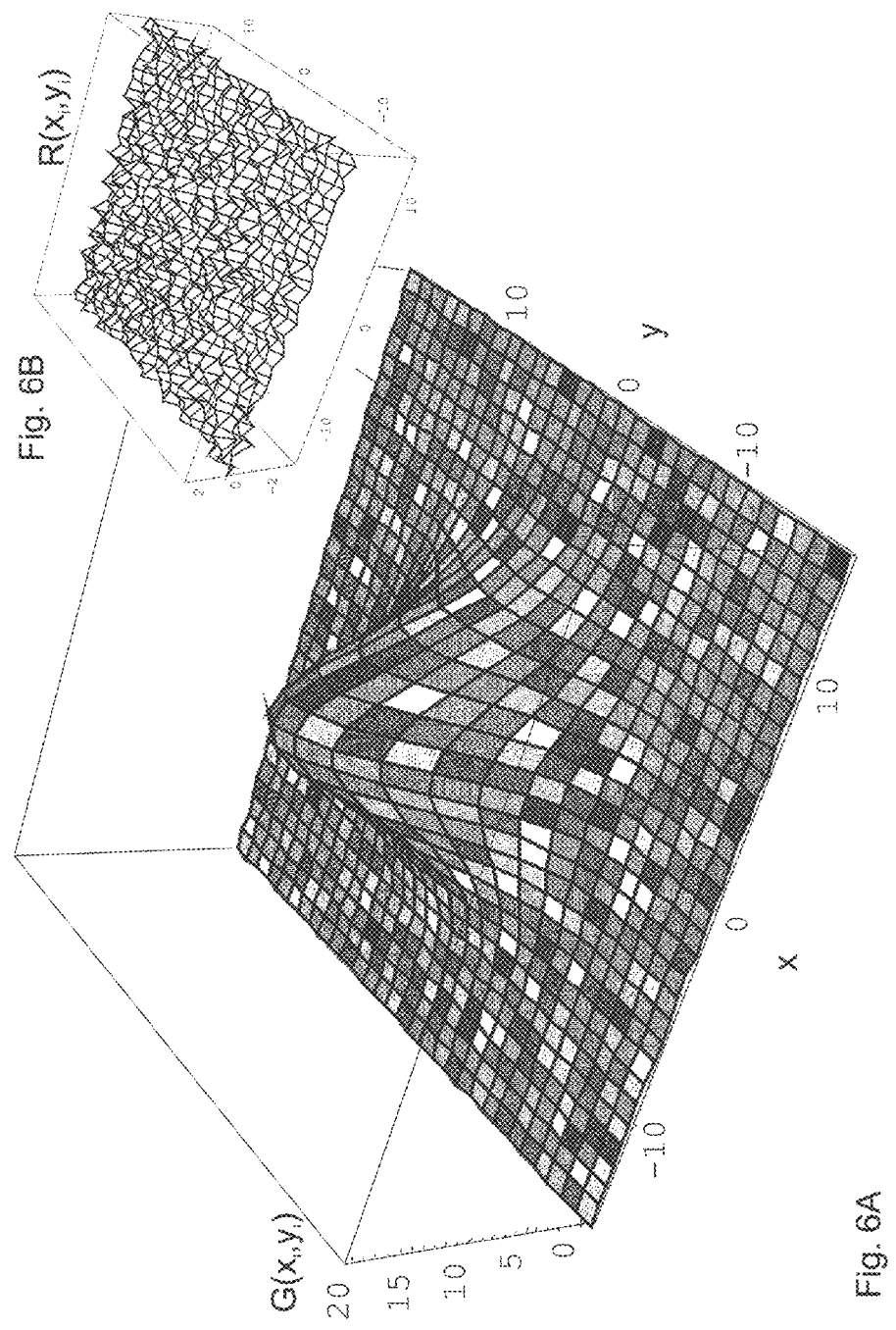

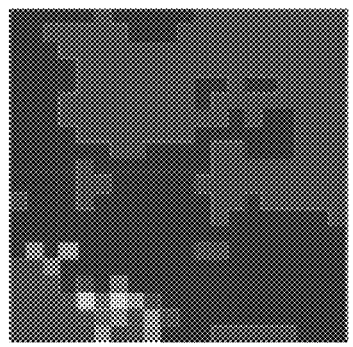 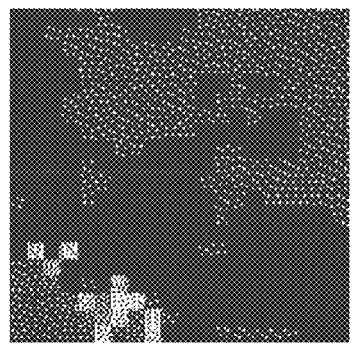
Fig. 7A
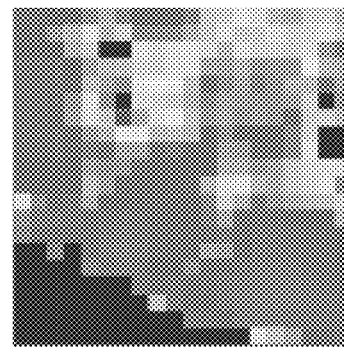 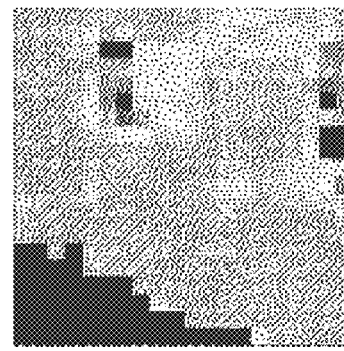
Fig. 7B
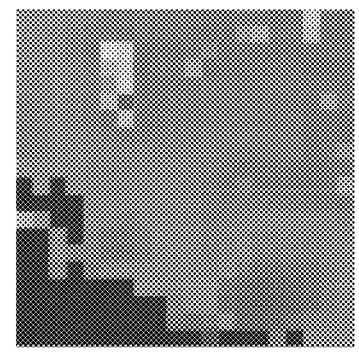 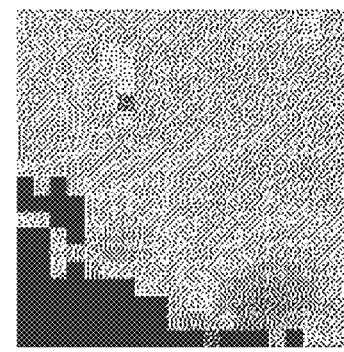
Fig. 7C

METHOD FOR EVALUATING FLUORESCENCE CORRELATION SPECTROSCOPY MEASUREMENT DATA

CROSS-REFERENCE TO RELATED APPLICATIONS

The present patent application is a continuation application of International Patent Application No. PCT/EP2009/006819, filed Sep. 22, 2009, which is based on, and claims priority to, German Patent Application No. 10 2008 049 877.7, filed Sep. 30, 2008, both of which are incorporated herein in their entireties by reference.

BACKGROUND OF THE INVENTION (1) Field of the Invention

The invention relates to a method for evaluating fluorescence measurement data in at least one-dimensional spatial resolution from a sample and a control unit for a laser scanning microscope.

(2) Description of Related Art Including Information Disclosed Under 37 CFR 1.97 and 1.98

Fluorescence correlation spectroscopy (FCS) can be used to examine variable substance concentrations in the microscopic range caused by diffusion and other transport processes in a sample. Physical and biological transport processes in or through a single volume having a diameter of about 200 nm can be observed in this way. Spatial resolution of microscopic transport processes is achieved by scanning fluorescence correlation spectrography (S-FCS), also referred to as image correlation spectroscopy (ICS). Time spans of seconds to minutes can be tracked.

Raster image correlation spectroscopy (RICS) allows tracking within a cell or between cells separated by a membrane in the microsecond and millisecond range in two or three-dimensional spatial resolution (Digman et al.: "Measuring Fast Dynamics in Solutions and Cells with a Laser Scanning Microscope" in "Biophysical Journal", Vol. 89, August 2005, pp. 1317-1327). The sample is optically scanned here in a two or three-dimensional grid. In the typical process, time series are recorded. It is advantageous to use a laser scanning microscope (LSM) for scanning correlation spectroscopy. During the optical scanning movement of a RICS measurement, digital sampling values are electronically recorded at a typically constant sampling frequency and further processed into pixel values. Each pixel value is determined from one or multiple sampling values. Scanning along the first scan direction is repeated along a second scan direction after the scanning beam has been shifted (scan gap) such that a series of pixel rows is recorded.

To be able to make statements about transport processes in a sample, correlation-spectroscopic measuring procedures are typically evaluated by determining correlations of the fluorescence measurement data such as auto or cross-correlations and by adapting mathematical transport models to these correlations, for example, by means of curve fittings. The adjusted models can be used to determine sample properties such as diffusion constants. The transport models are available in the form of mathematical functions, and the parameters of these functions are adjusted. Such correlation analyses with respect to RICS measurements are performed separately for several, typically overlapping, regions of the scan field. The determination of model parameters in each region, i.e. the determination of the spatial distribution of the model parameters within the sample, is called mapping. The results of correlation analyses can be presented graphically, e.g. using false colors.

It is a problem that areas can be contained in one or several sample regions that contain little or no information and therefore falsify the results of the analysis. For example, these can be dark, almost fluorescence-free areas in which noise is detected at best. It is possible in areas of low fluorescence that a correlation of measurement data of the corresponding sample region cannot be evaluated for lack of statistics. If sample properties such as a diffusion constant are determined in such sample regions despite their low information content, adapting the parameters of a model function by curve fitting will result in absurd values for the desired sample properties despite good adjustment quality. Values could be obtained for a diffusion constant that is too high by several orders of magnitude.

It is known from prior art that faulty fluorescence correlation analyses can be filtered out by comparing the adapted model function parameters, that is, the results of the curve fittings, to meaningful ranges of values. If the results are outside these ranges of values, they are discarded and not used for determining the desired sample properties. In addition to restricting the values to ranges, it is known to discard the results of curve fittings if the mean value deviations of the model function parameters exceed a preset threshold or if the ratio of the standard deviations of the model function parameters to their best values exceeds a predetermined threshold. All approaches listed above have the disadvantage that the meaningful ranges of values or the threshold values, respectively, have to be determined as so-called a priori knowledge in time-consuming test series. The rigid limitation to a specific range of values or thresholds diminishes the accuracy of the evaluation since statistically correct correlations that result in model parameter values outside the limits will be discarded. In addition, one or, if several sample regions are mapped, multiple elaborate and time-consuming curve fittings have to be performed before the results can be checked for meaningfulness.

The problem to be addressed by the invention therefore is that of providing a method and control unit of the types mentioned above with the help of which sample properties can be determined from fluorescence correlations in a simpler, faster and more accurate way.

BRIEF SUMMARY OF THE INVENTION

According to the invention, a degree of suitability for one or several regions of the sample for correlation analysis is determined. A quantity is considered a degree of suitability in accordance with the invention if it gives a quantitative description of the information content of the corresponding region or of the error to be expected in a correlation evaluation and can therefore be used as a criterion for filtering and/or selecting the corresponding region for a correlation analysis. In particular, it can be a scalar value, a multi-component vector, or a higher-order tensor. In other words, a characteristic value is determined for the corresponding region that quantifies its suitability for a correlation analysis. According to the invention, a quantitative check of data consisting of discrete points for similarity that takes translations among the data points into account is considered a correlation evaluation or correlation analysis.

The invention allows more refined filtering without requiring an elaborate and time-consuming curve fitting. Finer filtering allows higher accuracy when determining the sample properties. A decision whether to perform a curve fitting at all can then be made based on the degree of suitability determined. Some out of several regions can be selected for a curve fitting while others can be discarded in this way. Alternatively, curve fittings can be performed unconditionally for all regions and the corresponding degree of suitability for the correlation analysis can be stored as a quality characteristic in addition to the adapted model function parameters. In this way, the results can later be filtered by degree of suitability without having to perform another curve fitting. At any rate, filtering advantageously is not tied to the value associated with one or several specific model parameters. In particular, it will be possible to distinguish sample regions that are relevant for evaluation from non-relevant sample regions even before the elaborate curve fitting by advantageously determining the degree of suitability before performing a curve fitting for adapting a model function to the correlation. This cannot be done with the known methods, especially not in sample regions that only contain noise.

Advantageously, the degree of suitability is determined by determining one at least one-dimensional correlation with multiple correlation data points based on measurement data from the corresponding region and counting correlation points that show a statistically significant deviation from a comparative set within the correlation.

The invention can be applied both to spatial and temporal correlations. The number determined in this way is advantageously output or stored but it can also be processed immediately, such as in a decision on performing a curve fitting.

According to the invention, the number of significantly deviating correlation points in the corresponding correlation is used as the degree of suitability of that region. It represents a highly accurate statement about the information content of the corresponding sample region with respect to a correlation analysis, such as by means of a curve fitting.

Preferably, only a discontinuous or continuous series of neighboring correlation points that begin at the maximum of the correlation is counted. The most informative data points for a correlation analysis are in the area around the maximum of the correlation. The method is simplified and accelerated with almost unchanged accuracy by limiting the count to a linear region beginning at the maximum. While the maximum is at the origin of the coordinates in an autocorrelation, it can be at a distance from the coordinate origin in a cross-correlation so that the correlation maximum has to be determined before the count.

In a preferred embodiment, a proper subset of the correlation (i.e. its data points), especially a proper subset of a quadrant of the correlation, is used as the comparative set. The proper subset can be rectangular and, in particular, a square shape. This also helps to simplify and accelerate the method with almost unchanged accuracy. The corner point of the quadrant may also be the maximum of the correlation instead of the coordinate origin. Limitation to a maximum of one quadrant utilizes the fact that the information that is essential for detecting a shift is particularly contained in the fourth quadrant (relative to the correlation maximum).

It is advantageous for determining the significantly deviating correlation data points to determine a value of a statistical quantity within the comparative set and to find those correlation data points significantly deviating which have a value that exceeds a threshold that can be, or is, preset relative to the value of the statistical quantity. The informative data points can be found easily and quickly in this way.

Advantageously, a mean value of the comparative set is used as the statistical quantity and a multiple of a standard deviation of the mean value is used as the threshold value. These quantities can be determined with little computational effort and allow a highly precise statement about the information content of the data points.

In another embodiment of the invention, the degree of suitability is determined by determining an at least one-dimensional correlation with multiple correlation data points based on measurement data from the corresponding region, then calculating a ratio of positive to negative correlation values. The ratio of positive to negative correlation values is shifted in favor of the positive values in meaningful correlations with respect to a correlation analysis. Therefore the ratio of positive and negative values determines suitability for a correlation analysis. The ratio determined is advantageously output or stored but it can also be processed immediately, such as in a decision on performing a curve fitting. In addition to finding the statistically significant data points described above, the determined ratio can also be used for obtaining the degree of suitability of the region.

The ratio of positive and negative values is preferably obtained as the quotient of either the positive maximum value of the correlation and the negative minimum value of the correlation, or of the number of positive correlation values and the number of negative correlation values. These quotients can be calculated with little computational effort.

In a first embodiment, the corresponding degrees of suitability are determined for multiple regions, one of the regions is selected for a curve fitting based on the degrees of suitability, and the corresponding curve fitting is performed. This prevents unnecessary curve fittings that would only affect the result adversely.

In an alternative second embodiment, curve fittings are performed for multiple regions, and the corresponding degree of suitability is stored with the results of these curve fittings. This allows later filtering of the results of the curve fittings and determining the accuracy of the model parameters. It is advantageous to first record the correlation spectroscopy measurement data using a laser scanning microscope.

The invention also comprises a computer program that is set up for performing the method of the invention, and a control unit for a laser scanning microscope that is software-complemented for performing a method according to the invention, as well as a respectively equipped laser scanning microscope.

In particular, the invention includes a control unit for a laser scanning microscope, and said control unit determines a degree of suitability for a correlation analysis for evaluating fluorescence measurement data of a sample in at least one-dimensional spatial resolution.

BRIEF DESCRIPTION OF THE SEVERAL
VIEWS OF THE DRAWINGS

The invention will be explained in more detail below with reference to embodiments. The figures show the following:

FIGS. 6A and 6B show an adapted two-dimensional model function with residual errors; and FIGS. 7A-7C show resulting diffusion mappings without filtering, with prior art filtering, and with filtering according to the invention.

DETAILED DESCRIPTION OF THE INVENTION

Figure 1:
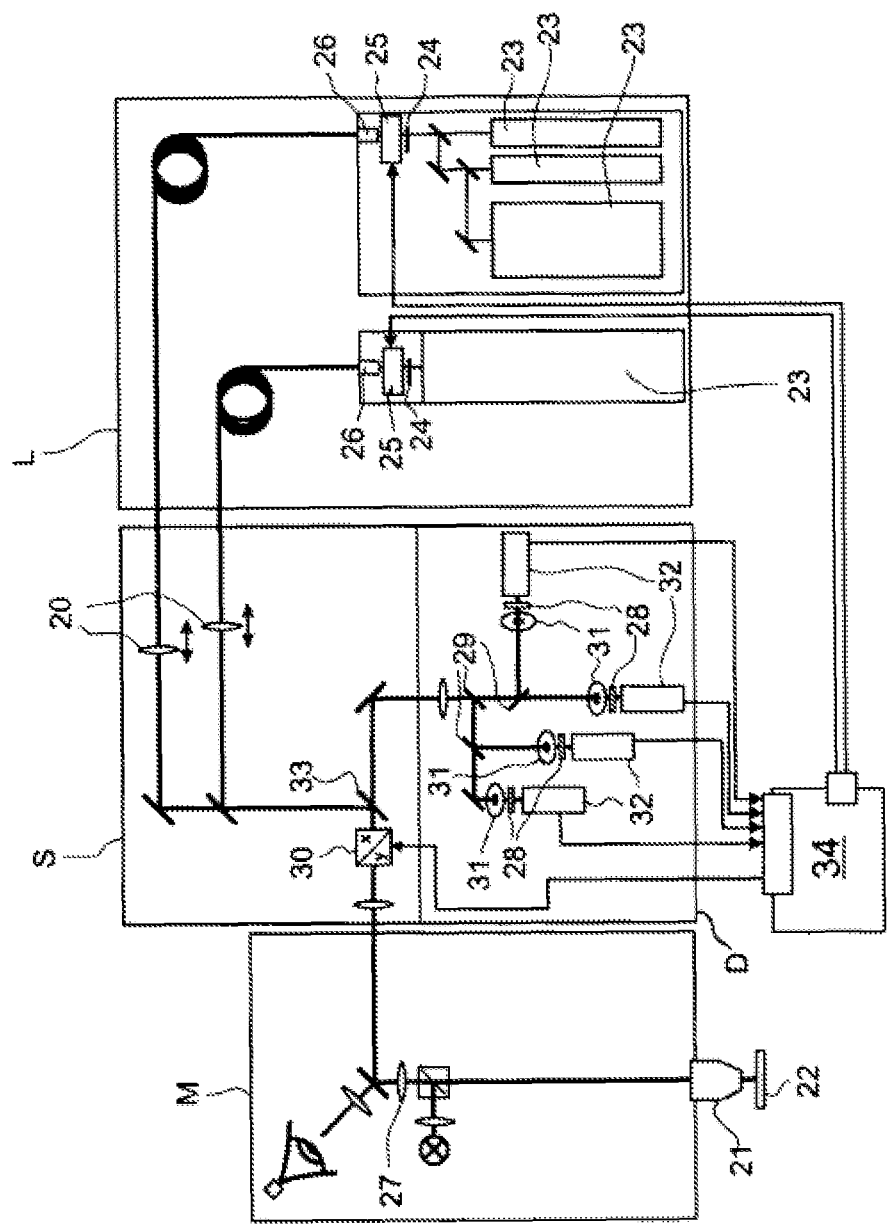
FIG. 1 shows a block diagram of a laser scanning microscope.

In describing preferred embodiments of the present invention illustrated in the drawings, specific terminology is employed for the sake of clarity. However, the invention is not intended to be limited to the specific terminology so selected, and it is to be understood that each specific element includes all technical equivalents that operate in a similar manner to accomplish a similar purpose.

FIG. 1 is a diagrammatic view of an LSM (Laser Scanning Microscope) that is controlled using a control unit 34. The LSM is of modular design and consists of a lighting module L with lasers 23, a scanning module S, a detection module D, and the microscope unit M with a microscopic lens 21. The control unit 34 can influence the light from the lasers 23 through barn doors (literally, "light valves" or "light flaps") 24 and attenuators 25 before it is fed via optical fibers and coupling optics 20 into the scan unit S and concentrated there. The light passes via the main beam splitter 33 and the X-Y scanning unit 30 comprising two galvanometer mirrors through the microscopic lens 21 towards the sample 22 where it lights a focus volume (not shown).

Light reflected from the sample or emitted fluorescent light is conducted through the microscopic lens 21 via the scanning unit S and through the main beam splitter 30 into the detection module D. The main beam splitter 30 may for example be designed as a dichroic color splitter for fluorescence detection. The detection module D comprises multiple detection channels that are separated by color splitters 29, each of said channels with a pinhole diaphragm 31, a filter 28, and a photomultiplier 32. Slotted diaphragms (not shown) may be used instead of pinhole diaphragms 31, e.g. when there is line lighting. The confocal pinhole or slotted diaphragms 31 are used to discriminate sample light that does not originate from the focus volume. The photomultipliers 32 therefore only detect light from the focus volume. The scanning unit 30 can be used to move the confocally lit and recorded focus volume of the sample 22 over the sample 22 to record a pixel-by-pixel image by turning the galvanometer mirrors of the scanning unit 30 in a defined way. The control unit 34 directly controls both the movement of the galvanometer mirrors and the switching of the lighting using the barn doors 24 or attenuators 25. The data from the photomultipliers 32 is also recorded via the periphery interface.

Figure 2:
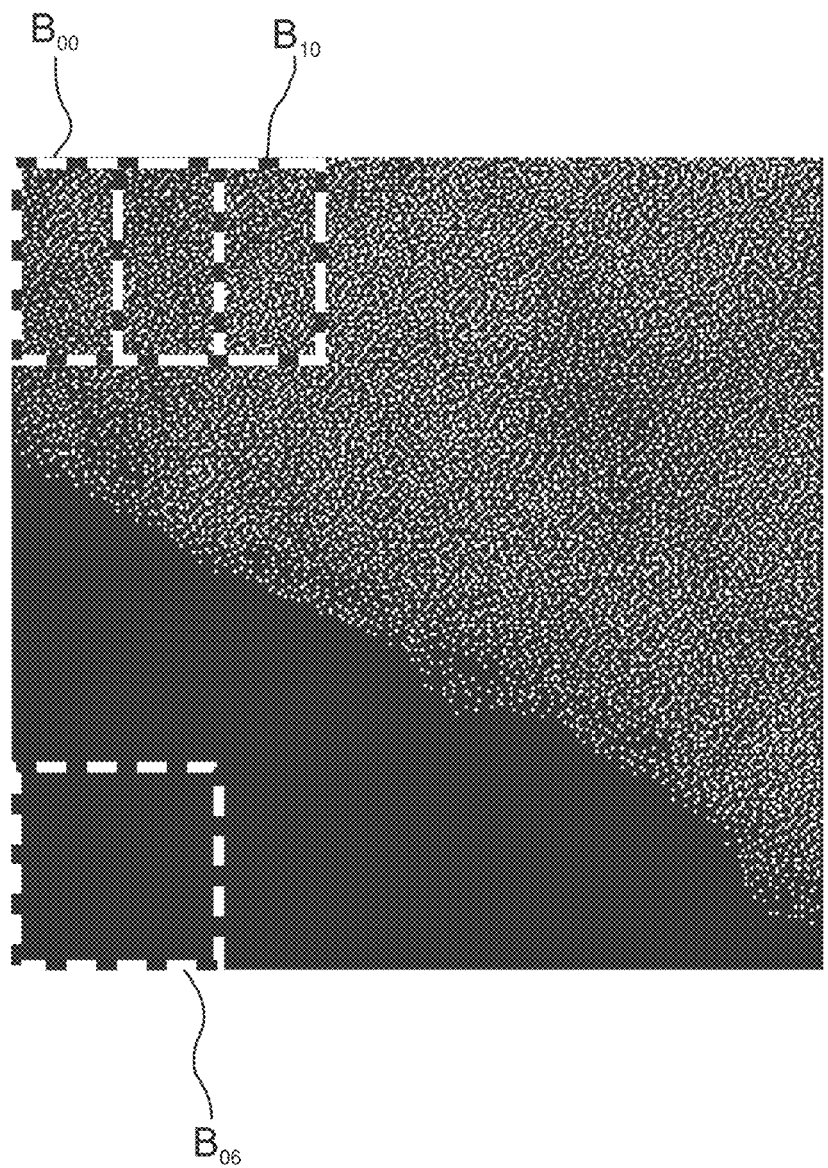
FIG. 2 shows a confocal fluorescence recording of the edge region of a cell.

FIG. 2 shows a fluorescence recording in the edge region of a biological cell as sample 22 with an exemplary image size of 512×512 pixels for which the photomultipliers 32 were operated in photon count mode. The image was rasterized in black and white for better visibility. The cell edge stretches in an approximate diagonal from the top left to the bottom right part of the image. It is obvious that the bottom left portion of the image does not contain information and that the fluorescence activity in the top right portion of the image is distributed unevenly. For an example of a diffusion mapping, the image is divided into multiple regions $B_{mn}$ of the same size, for example 128×128 pixels, and a diffusion constant is to be determined by correlation analysis for each of these regions. These regions may overlap. At an overlap of one half in horizontal and vertical direction, there will be 49 sample regions (m=0 . . . 6; n=0 . . . 6) to be evaluated.

Figure 3:
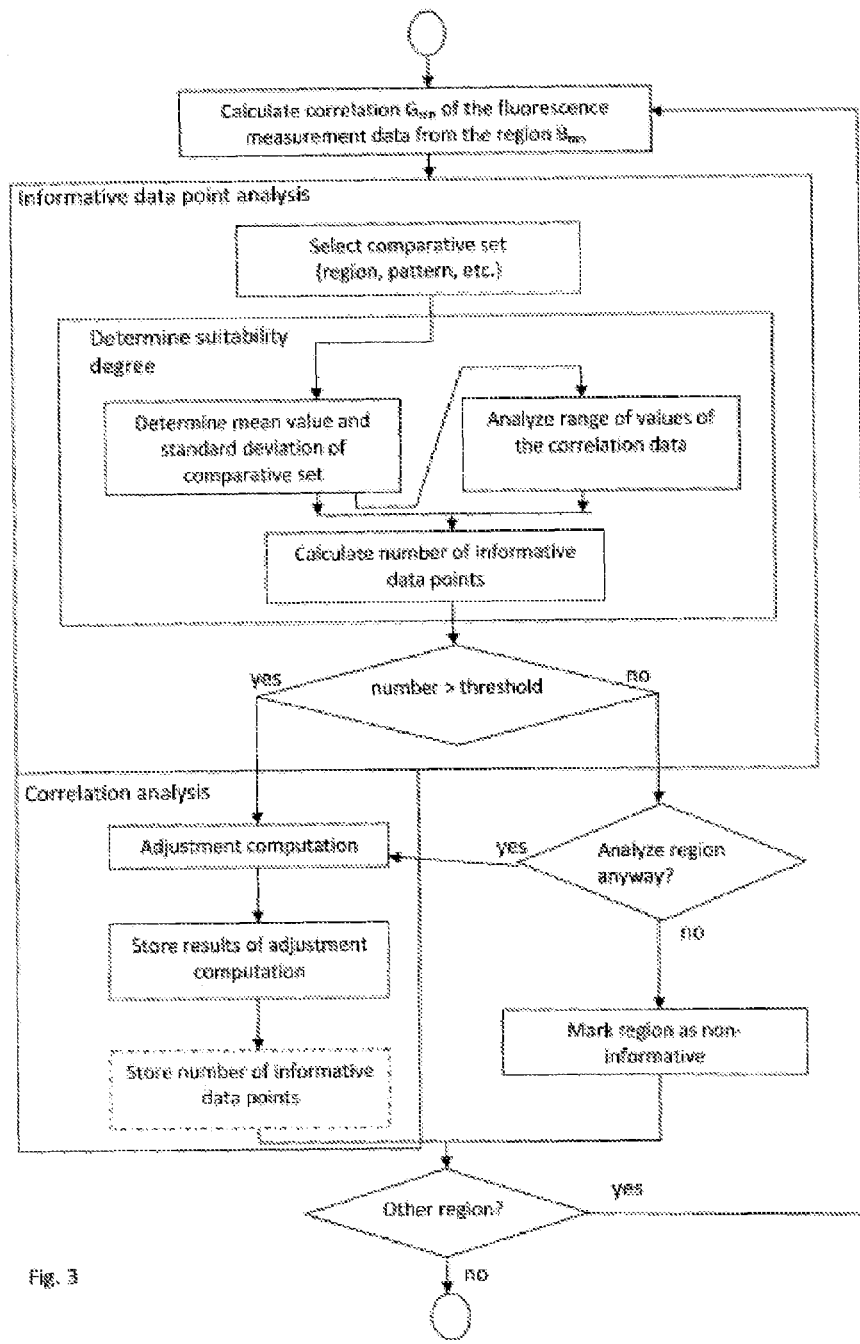
FIG. 3 shows a flow chart of an evaluation method according to the invention.

FIG. 3 shows an exemplary embodiment of the method according to the invention in the form of a flow chart. For each sample region $B_{mn}$, a separate two-dimensional correlation $G_{mn}$ such as the autocorrelation of the corresponding region is calculated from the intensity values of the pixels. Each correlation consists of a two-dimensional set of i=0 . . . (r×s), e.g. 0 . . . 128×128 data points $(x_i,y_i)$ having a value $G_{mn}(x_i,y_i)$ that can be graphically represented along a third coordinate or by color coding. Alternatively, one-, three-, or multidimensional correlations with a corresponding set of data points can be used.

Figure 4A:
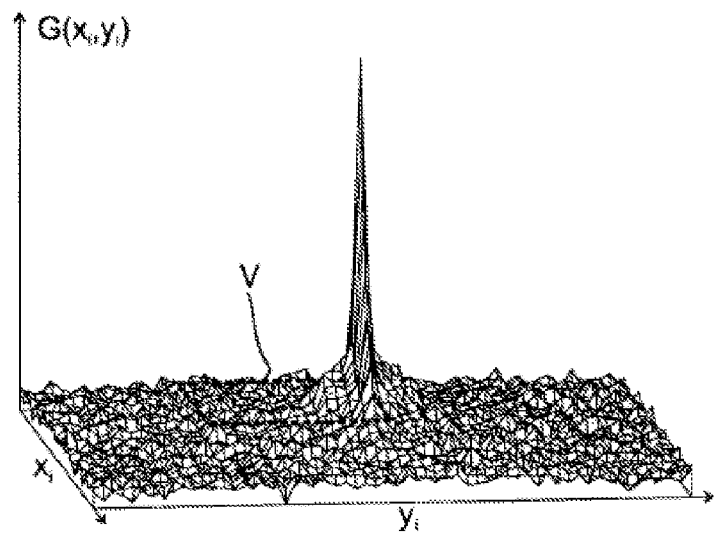
FIGS. 4A and 4B show a correlation of a slow diffusion process.
Figure 4B:
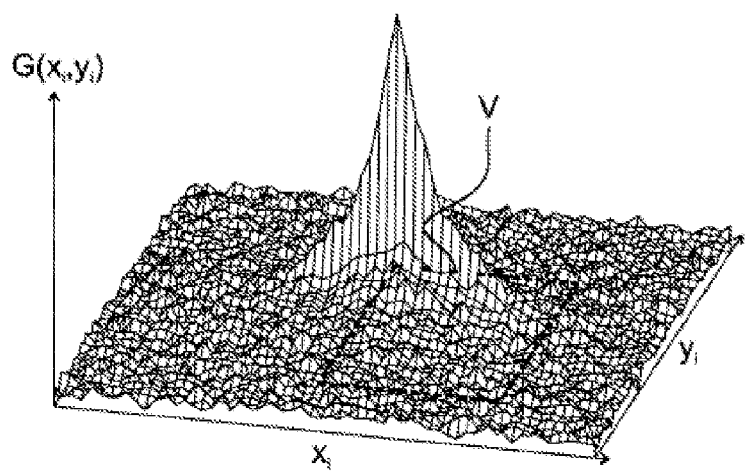

FIGS. 4A and 4B and FIGS. 5A and 5B show two examples of correlations $G(x_i,y_i)$ in pseudo-3D representation. The partial figures each show different viewing angles. The coordinate origin of correlation G is in the maximum of the correlation. The correlation shown in FIGS. 4A and 4B represents a slow diffusion process, which is apparent from the flat incline both in x and in y direction. The correlation shown in FIGS. 5A and 5B however represents a fast diffusion process since it drops sharply in y direction.

Figure 5A:
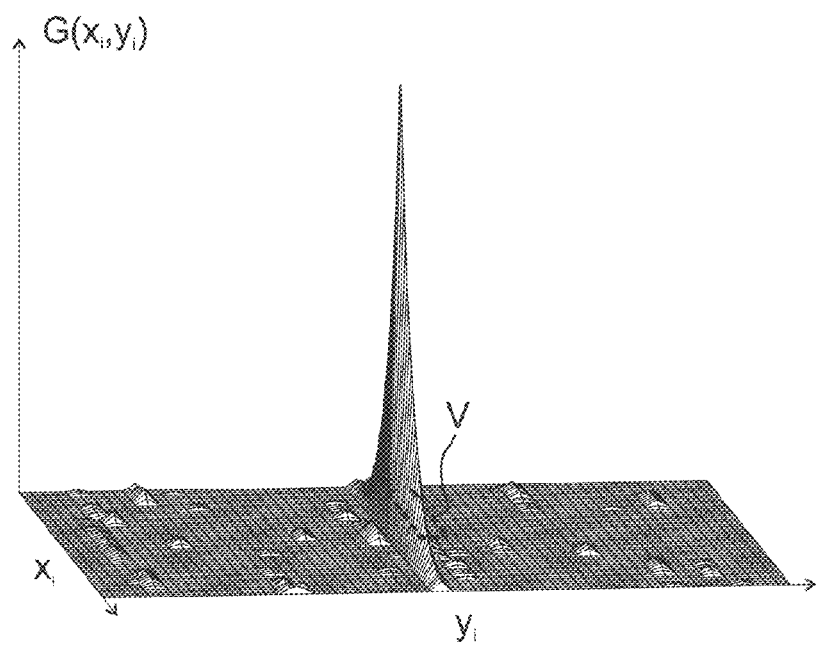
FIGS. 5A and 5B show a correlation of a fast diffusion process.
Figure 5B:
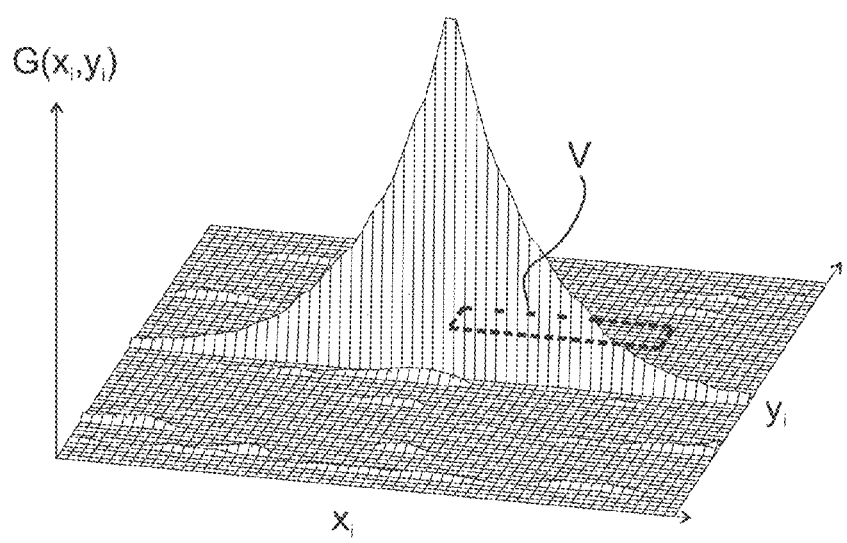

According to the method depicted in FIG. 3, an informative data point analysis is then performed for each region $B_{mn}$ of the mapping to determine a degree of suitability of the corresponding region $B_{mn}$. The informative data point analysis initially consists in the selection of a statistically representative comparative set V from the correlation data points $G_{mn}(x_i,y_i)$. For example, a region of 80×80 data points $(x_i,y_i)$ is selected as comparative set V. For illustration, FIGS. 4A and 4B show a square comparative set V as delineated by a broken line. This is a proper subset of the fourth quadrant of the correlation G. Alternatively, the full quadrant or an even larger region could be used as the comparative set. It is advantageous to limit the size of the comparative set, e.g. to 80×80 data points. If in principle a full quadrant is used and the correlation size is 128×128 data points, the comparative set V would be 64×64. However only an 80×80 comparative set is used for a correlation size of 256×256 due to the limit. FIGS. 5A and 5B indicate an alternative form of a comparative V in the same way as in FIGS. 4A and 4B. It is a continuous series of neighboring correlation data points that begins in the coordinate origin at the maximum of correlation G. Alternatively, individual points from such a series can be used as comparative set.

As an alternative to a single rectangular region, the comparative set can be composed of multiple disjunctive sections of correlation data of regular or irregular shape that are selected at random or based on a predefined pattern. For example, a regular chessboard pattern or a random distribution of single points $(x_i,y_i)$ could be used in the two-dimensional case, and an interrupted cubic pattern in the three-dimensional approach. The comparative set can be selected automatically or based on a predefined pattern. Alternatively, the user can determine the type, shape, orientation and size of the comparative set.

After the comparative set has been selected automatically, two statistical parameters of the comparative set are determined in a first step for determining the degree, namely the arithmetic mean and the standard deviation of the comparative set. In an additional step, the value range of the correlation data points can optionally be examined for a ratio of positive data points $G_{mn}(x_i,y_i)>0$ to negative data points $G_{mn}(x_i,y_i)<0$ in a predefined window of the correlation $G_{mn}$, which can be used as an indication for determining the degree. The window checked for the value range can for example be located along the x axis of the correlation $G_{mn}$. The ratio can be determined mathematically as the difference or quotient of the number of positive and the number of negative data points. The minimum and maximum values of the correlation can be compared in lieu of their number. For example, if the numbers coincide or the minimum and maximum values are of the same magnitude, the degree of suitability is arbitrarily set to zero. A degree of suitability that was determined based on the statistical parameters only can later be scaled based on the resulting ratio. Alternatively, only the determined ratio can be used as degree of suitability, e.g. by appropriate scaling to a comparable number of pixels.

In general, the number of those data points $(x_i,y_i)$ for which the value $G_{mn}(x_i,y_i)$ significantly deviates from the comparative set can be used as a degree of suitability of the examined region $B_{mn}$. These data points $(x_i,y_i)$ can be determined using the statistical parameters of the comparative set, for example by comparing the correlation value $G_{mn}(x_i,y_i)$ to the mean value of the comparative set. It is checked, for example, if the correlation value $G_{mn}(x_i,y_i)$ is more than twice the standard deviation above the mean value. If this condition applies, the corresponding data point $(x_i, y_i)$ is considered to be informative for a correlation analysis because it significantly deviates from the comparative set. The number of informative data points $(x_i,y_i)$ in the correlation $G_{mn}$ that were determined successively in this way will be utilized as degree of suitability at the end of the informative data analysis. The degree of suitability is compared to a threshold value that the user can preset. For example, a curve fitting will be performed and its result stored only if the degree of suitability is greater than the threshold value. If the degree of suitability is lower, the user is explicitly asked in the example shown if a curve fitting should be performed anyway. In other embodiments the user is not asked in this case but region $B_{mn}$ is automatically marked non-informative, and the method continues with the next region.

It was found, according to the invention that determining informative data points can also advantageously be limited to a predefined window in the correlation $G_{mn}$, e.g. to data points along the x-axis of the correlation $G_{mn}$, such as a maximum of 30 directly adjacent data points, wherein the examination and count is started next to the origin at data point $G_{mn}(1,0)$. Such a window can help to determine the degree of suitability quickly and at sufficiently high accuracy since a correlation curve should drop over a range of ten to thirty data points to obtain a good evaluation using an adjustment calculation. Advantageously, the data point at the origin, $G_{mn}(0,0)$, is generally left out because it does not have informative value. If the correlation drops immediately after the origin value $G_{mn}(0,0)$, this indicates that only noise was recorded in the corresponding sample region $B_{mn}$. It is preferred that an uninterrupted series of adjacent correlation points along the x-axis is examined, but patterns with a specific (e.g. non-linear) function can be used for selecting data points to be examined. The comparative set should at any rate be statistically relevant and make up a substantial portion of the corresponding correlation $G_{mn}$.

The informative data point analysis and, optionally, the correlation analysis may be performed regardless of the resulting degrees for all regions $B_{mn}$ and stored together with the corresponding degree of suitability for later filtering. In an alternative embodiment, the correlation analysis may be performed regardless of the resulting degrees for all regions $B_{mn}$ and stored together with the corresponding degree of suitability for later filtering.

In addition or as an alternative to mean value and standard deviation, other statistical parameters can be derived from the comparative set and used in the conditions for the values of the individual correlation data points in order to determine data points $(x_i,y_i)$ that deviate statistically significantly from the comparative set.

FIGS. 6A and 6B show an adapted two-dimensional model function $G_{mn}(x_i,y_i)$ (partial FIG. 6A) in pseudo-3D with residual errors $R_{mn}(x_i,y_i)$ (partial FIG. 6B). The model function shown is merely an example.

FIGS. 7A-7C show examples of diffusion mappings that were determined from the fluorescence image of FIG. 2 using different evaluation methods. The mappings in the left column are color-coded, and the right column shows a corresponding black-and-white grid. Partial FIG. 7A shows an unfiltered mapping. It is apparent that extremely high diffusion coefficients are assigned to some regions outside the cells due to the forced curve fitting while no meaningful diffusion coefficients can be detected in vast parts of the cell due to the necessary scaling of the false colors. Partial FIG. 7B shows a mapping that was subsequently filtered for the model parameter values. The known filtering based on model parameters for example removes the regions shown black in the interior of the cell although these regions have a normal drop in correlation. While this can be improved by setting specific filtering limits, it is very time-consuming to determine these. Partial FIG. 7C finally shows the result of a filtering based on degrees of suitability determined according to the invention, for example the number of informative correlation data points in the corresponding region $B_{mn}$. The degrees of suitability allow highly accurate filtering that omits no regions $B_{mn}$ inside the cell and still correctly determines the transition to the non-informative regions $B_{mn}$.

Advantageously, the user can predefine the size and overlap or the number of regions $B_{mn}$ to be mapped as well as the specific sample model and individual model parameters.

Fluorescence image data can be filtered onto immobile structures in a preprocessing step. Bleaching is also possible. After mapping the visual representation of the adapted model parameters or derived quantities can for example be filtered based on degrees and/or other criteria. For example, filtering can be performed based on threshold values for individual or multiple adapted model parameters of for the ratio of the standard deviation of the model parameters to the model parameter values.

Modifications and variations of the above-described embodiments of the present invention are possible, as appreciated by those skilled in the art in light of the above teachings. It is therefore to be understood that, within the scope of the appended claims and their equivalents, the invention may be practiced otherwise than as specifically disclosed.

What is claimed is:

1. A control unit for a laser scanning microscope comprising a lighting module, a scanning module, a microscope module, and a detection module, wherein light is transmitted from the lighting module to the scanning module, light passes via the scanning module through the microscope module to confocally illuminate a focus volume of a sample (22), light reflected from the sample or fluorescence emitted from the focus volume passes via the scanning module to the detection module, and the fluorescence emitted from the focus volume is recorded as an image having fluorescence measurement data associated therewith, wherein:

said control unit controls the lighting module and the scanning module, divides the image of the focus volume of the sample (22) into a plurality of image regions corresponding to regions ($B_{mn}$) of the sample, and distinguishes regions of the sample that are relevant for evaluating the fluorescence measurement data recorded in the recording step from regions of the sample that are non-relevant by determining a degree of suitability for at least one of the regions ($B_{mn}$) of the sample (22), wherein the degree of suitability quantifies the suitability of a corresponding region for a correlation analysis for evaluating the fluorescence measurement data of the sample (22).

2. A method for evaluating fluorescence measurement data of a sample using the control unit of claim 1, wherein the data have spatial resolution in at least one dimension, the method comprising the steps of:
confocally lighting a focus volume in the sample to cause the emission of fluorescence from the focus volume,
recording the fluorescence emitted from the focus volume as an image having fluorescence measurement data associated therewith,
dividing the image of the sample into a plurality of image regions corresponding to regions ($B_{mn}$) of the sample;
distinguishing regions of the sample that are relevant for evaluating the fluorescence measurement data recorded in the recording step from regions of the sample that are non-relevant by determining a degree of suitability for at least one of the regions ($B_{mn}$) of the sample, wherein the degree of suitability quantifies the suitability of a corresponding region for a correlation analysis for evaluating the fluorescence measurement data recorded in the recording step.

3. The method according to claim 2 wherein the following steps are performed for determining the degree of suitability:
determining an at least one-dimensional correlation with multiple correlation data points ($G_{mn}(x_i, y_i)$) based on measurement data from a corresponding region selected from the plurality of regions ($B_{mn}$); and
counting of correlation data points ($G_{mn}(x_i, y_1)$) that statistically significantly deviate from a comparison set within the correlation ($G_{mn}$).

4. The method according to claim 3, wherein the number of significantly deviating correlation data points ($G_{mn}(x_i, y_i)$) in the corresponding correlation ($G_{mn}$) counted in the counting step is determined for the corresponding region, and the number quantifies the degree of suitability of the corresponding region.

5. The method according to claim 3, wherein only a number of neighboring correlation data points ($G_{mn}(x_i, y_1)$) are counted beginning at the coordinate origin ($G_{mn}(0,0)$) of the correlation ($G_{mn}$).

6. The methods according to claim 3, wherein a proper subset of the correlation ($G_{mn}$) is used as the comparative set.

7. The methods according to claim 6, wherein a proper or improper subset of a quadrant of the correlation ($G_{mn}$) is used as the comparative set.

8. The method according to claim 3, wherein a value of a statistical quantity within the comparison set is determined and those correlation data points ($G_{mn}(xi, yi)$) are found to be significantly deviating which have a value that exceeds a threshold value that can be, or is, preset relative to the value of a statistical quantity.

9. The method according to claim 8 wherein a mean value of the comparison set is used as the statistical quantity and a multiple of a standard deviation of the mean value is used as the threshold value.

10. The method according to claim 3 wherein the following steps are performed for determining the degree of suitability:
determining an at least one-dimensional correlation with multiple correlation data points based on measurement data from a corresponding region selected from the several regions; and
determining a ratio of positive to negative correlation values ($G_{mn}(x_i, y_i)$).

11. The method according to claim 10, wherein the ratio is determined as either the quotient of the positive maximum value of the correlation ($G_{mn}$) and the negative minimum value of the correlation ($G_{mn}$), or as the quotient of the number of positive correlation values and the number of negative correlation values.

12. The method according to claim 10, wherein in the step of distinguishing regions of the sample, the degree of suitability of the region ($B_{mn}$) is quantified by determining the ratio of positive to negative correlation values in the corresponding correlation.

13. The method according to claim 2, further comprising the step of performing a curve fitting for adapting a model function to the correlation, following the step of distinguishing regions of the sample.

14. The method according to claim 13, wherein in the step of distinguishing regions of the sample, a corresponding a degree of suitability is determined for multiple regions ($B_{mn}$) and the method further comprises the steps of:
selecting at least one of the regions ($B_{mn}$) for the curve fitting based on corresponding degrees of suitability determined in the step of distinguishing regions of the sample; and
performing the corresponding curve fitting.

15. The method according to claim 2, further comprising the step of:
performing curve fittings for multiple regions ($B_{mn}$), following the step of distinguishing regions of the sample; and
storing the corresponding degree of suitability with the results of the curve fittings.

16. The method according to claim 2, further comprising the step of recording correlation spectroscopy measurement data using a laser scanning microscope.

17. The method according to claim 2, wherein in the step of recording, the fluorescence emitted from the focus volume is recorded as a pixel-by-pixel image, wherein the fluorescence measurement data are associated with the pixels, and wherein the method comprises the further step of the control unit calculating a correlation from the fluorescence measurement data of the pixels in the at least one region ($B_{mn}$).

18. The control unit according to claim 1, wherein the control unit:
determines an at least one-dimensional correlation with multiple correlation data points based on measurement data from the corresponding region;
counts correlation data points that deviate statistically significantly from a comparison set within the correlation; and
at least one of outputs and stores the number determined as the degree of suitability.

19. The control unit according to claim 1, wherein the fluorescence emitted from the focus volume is recorded by the detection module as a pixel-by-pixel image, the fluorescence measurement data are associated with the pixels, and the control unit calculates a correlation from the fluorescence measurement data of the pixels in the at least one region ($B_{mn}$).

20. A laser scanning microscope comprising:
a control unit;
a lighting module;
a scanning module;
a microscope module; and
a detection module;
wherein:
light is transmitted from the lighting module to the scanning module;
light passes via the scanning module through the microscope module to confocally illuminate a focus volume of a sample;

light reflected from the sample or fluorescence emitted from the focus volume passes via the scanning module to the detection module;

the fluorescence emitted from the focus volume is recorded as an image by the detection module; and the control unit controls the lighting module and the scanning module, divides the image of the focus volume of the sample into a plurality of image regions corresponding to regions ($B_{mn}$) of the sample, and distinguishes regions of the sample that are relevant for evaluating the fluorescence measurement data recorded in the recording step from regions of the sample that are non-relevant by determining a degree of suitability for at least one of the regions ($B_{mn}$) of the sample, wherein the degree of suitability quantifies the suitability of a corresponding region for a correlation analysis for evaluating the fluorescence measurement data of the sample.

21. The laser scanning microscope according to claim 20, wherein the detection module records the fluorescence emitted from the focus volume as a pixel-by-pixel image, the fluorescence measurement data are associated with the pixels, and the control unit calculates a correlation from the fluorescence measurement data of the pixels in the at least one region ($B_{mn}$).

* * * * *